(12) United States Patent
Lee et al.

(10) Patent No.: US 11,733,546 B1
(45) Date of Patent: Aug. 22, 2023

(54) WIRELESSLY LOADED IMPEDANCE SENSOR FOR SELF-TEST

(71) Applicant: Verily Life Sciences LLC, South San Francisco, CA (US)

(72) Inventors: Shungneng Lee, Sunnyvale, CA (US); Tong Zhang, San Mateo, CA (US)

(73) Assignee: Verily Life Sciences LLC, South San Francisco, CA (US)

(*) Notice: Subject to any disclaimer, the term of this patent is extended or adjusted under 35 U.S.C. 154(b) by 774 days.

(21) Appl. No.: 16/803,767

(22) Filed: Feb. 27, 2020

Related U.S. Application Data

(60) Provisional application No. 62/812,443, filed on Mar. 1, 2019.

(51) Int. Cl.
| | | |
|---|---|---|
| *G02C 7/08* | (2006.01) | |
| *G01R 31/302* | (2006.01) | |
| *A61B 5/277* | (2021.01) | |
| *A61B 5/00* | (2006.01) | |

(Continued)

(52) U.S. Cl.
CPC ............. *G02C 7/083* (2013.01); *A61B 5/0024* (2013.01); *A61B 5/277* (2021.01); *A61B 5/398* (2021.01); *A61B 5/6821* (2013.01); *G01N 27/041* (2013.01); *G01N 27/045* (2013.01); *G01R 31/302* (2013.01); *G02C 7/04* (2013.01); *A61B 5/053* (2013.01); *A61B 2560/0223* (2013.01); *A61B 2562/0209* (2013.01); *A61B 2562/04* (2013.01)

(58) Field of Classification Search
CPC ....... A61B 3/00; A61B 3/0016; A61B 3/0025; A61B 3/0033; A61B 3/0075; A61B 3/1005; A61B 3/101; A61B 5/0024; A61B 5/053; A61B 5/277; A61B 5/6821; A61B 5/297; G01R 19/16566; G01R 31/00; G01R 31/2812; G01R 31/302; G01R 31/66; G01R 31/304; G01R 28/02

See application file for complete search history.

(56) References Cited

U.S. PATENT DOCUMENTS

| | | | |
|---|---|---|---|
| 6,123,668 | A | 9/2000 | Abreu |
| 8,608,310 | B2 | 12/2013 | Otis et al. |

(Continued)

OTHER PUBLICATIONS

Al-Gayem, Q., Liu, H., Richardson, A.., Burd, N., Test Strategies for Electrode Degradation in Bio-Fluidic Microsystems, 2011, J Electron Test, 27:57-68.DOI 10.1007/s10836-010-5180-9 (Year: 2011).*

(Continued)

*Primary Examiner* — Eun Hwa Kim
(74) *Attorney, Agent, or Firm* — Christensen O'Connor Johnson Kindness PLLC

(57) ABSTRACT

An apparatus with a built-in self-test includes a sensor electrode, an impedance sensor coupled to the sensor electrode to measure a test impedance of the sensor electrode as influenced by an external load, a secondary electrode disposed adjacent to the sensor electrode to inductively couple with the sensor electrode and influence the external load on the sensor electrode, a first switch coupled to the secondary electrode to selectively change a second impedance of the secondary electrode, and a controller coupled to the impedance sensor and the first switch. The controller includes logic for adjusting the first switch to wirelessly load the sensor electrode with the secondary electrode in a predetermined impedance state, measuring the test impedance with the impedance sensor while the secondary electrode is in the predetermined impedance state, and comparing the measured test impedance against a threshold impedance range to perform a self-test.

22 Claims, 8 Drawing Sheets

(51) Int. Cl.
*G01N 27/04* (2006.01)
*A61B 5/398* (2021.01)
*A61B 5/053* (2021.01)
*G02C 7/04* (2006.01)

(56) References Cited

U.S. PATENT DOCUMENTS

| | | | |
|---|---|---|---|
| 8,857,983 | B2 | 10/2014 | Pugh et al. |
| 8,870,370 | B1 | 10/2014 | Otis et al. |
| 9,192,298 | B2 | 11/2015 | Bouwstra et al. |
| 9,259,309 | B2 | 2/2016 | Fehr et al. |
| 9,825,364 | B2 | 11/2017 | O'Driscoll |
| 2006/0217775 | A1* | 9/2006 | Mills et al. .......... A61N 1/3925 128/897 |
| 2010/0295551 | A1* | 11/2010 | Hölzl ................ G01N 27/9086 324/694 |
| 2013/0218270 | A1 | 8/2013 | Blanckaert et al. |
| 2013/0258275 | A1 | 10/2013 | Toner et al. |
| 2014/0107448 | A1 | 4/2014 | Liu et al. |
| 2015/0305643 | A1* | 10/2015 | Negi et al. .......... A61B 5/6846 29/854 |
| 2015/0362755 | A1* | 12/2015 | Lee et al. ................ G02C 7/04 351/159.73 |
| 2015/0364822 | A1* | 12/2015 | O'Driscoll ............. H01Q 7/005 343/718 |
| 2016/0097833 | A1* | 4/2016 | Han et al. .......... G01R 29/0878 343/702 |
| 2017/0097520 | A1 | 4/2017 | Lee |
| 2018/0031867 | A1 | 2/2018 | Lee et al. |

OTHER PUBLICATIONS

Uddin et al., "UHF RFID Antenna architectures and applications", Scientific Research and Essays Vol. 5(10), pp. 1033-1051, May 18, 2010.

Liao et al., "A 3-μ W CMOS Glucose Sensor for Wireless Contact-Lens Tear Glucose Monitoring", IEEE Journal of Solid-State Circuits, Vol. 47, No. 1 Jan. 2012, 10 pages.

Lin et al., "Fabrications and Performance of Wireless LC Pressure Sensors through LTCC Technology", Sensors, 2018, 18, 340; DOI:10.3390/s18020340.

Liu, H., Richardson, A., Harvey, T.G., Ryan, T., Pickering, C., Embedded Test & Health Monitoring Strategies for Bio-Fluidic Microsystems, 2008, Electronics System-Integration Technology Conference, pp. 427-434.doi: 10.1 109/ESTC.2008.4684386 (Year: 2008).*

* cited by examiner

WIRELESSLY LOADED IMPEDANCE SENSOR FOR SELF-TEST

CROSS-REFERENCE TO RELATED APPLICATIONS

This application claims the benefit of U.S. Provisional Application No. 62/812,443, filed Mar. 1, 2019, which is hereby incorporated by reference in its entirety.

TECHNICAL FIELD

This disclosure relates generally to impedance sensor testing, and in particular, relates to self-testing of an impedance sensor.

BACKGROUND INFORMATION

Accommodation is a process by which the eye adjusts its focal distance to maintain focus on objects of varying distance. Accommodation is a reflex action, but can be consciously manipulated. Accommodation is controlled by contractions of the ciliary muscle. The ciliary muscle encircles the eye's elastic lens and applies a force on the elastic lens during muscle contractions that change the focal point of the elastic lens.

As an individual ages, increased stiffness of the eyes' lenses tend to decrease the effectiveness of the ciliary muscles in providing accommodation. Presbyopia is a progressive age-related loss of accommodative or focusing strength of the eye, which results in increased blur at near distances. This loss of accommodative strength with age has been well studied and is relatively consistent and predictable. Presbyopia affects nearly 1.7 billion people worldwide (110 million in the United States alone) and that number is expected to substantially rise as the world's population ages.

Recent technologies have begun to provide for various devices that operate in or on a human eye to aid the visual focus of a user. For some types of these devices, an accommodating lens includes one or more elements and circuitry to apply an electrical signal to change a focusing/optical power of the one or more elements. Determining when to change such focusing power may be based on, or correlated to, a direction of a gaze by a user of the optical device. It is important to include built-in self-test mechanisms to ensure the accommodation control mechanisms are functional, and quickly identify any defects.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

DETAILED DESCRIPTION

Figure 1:
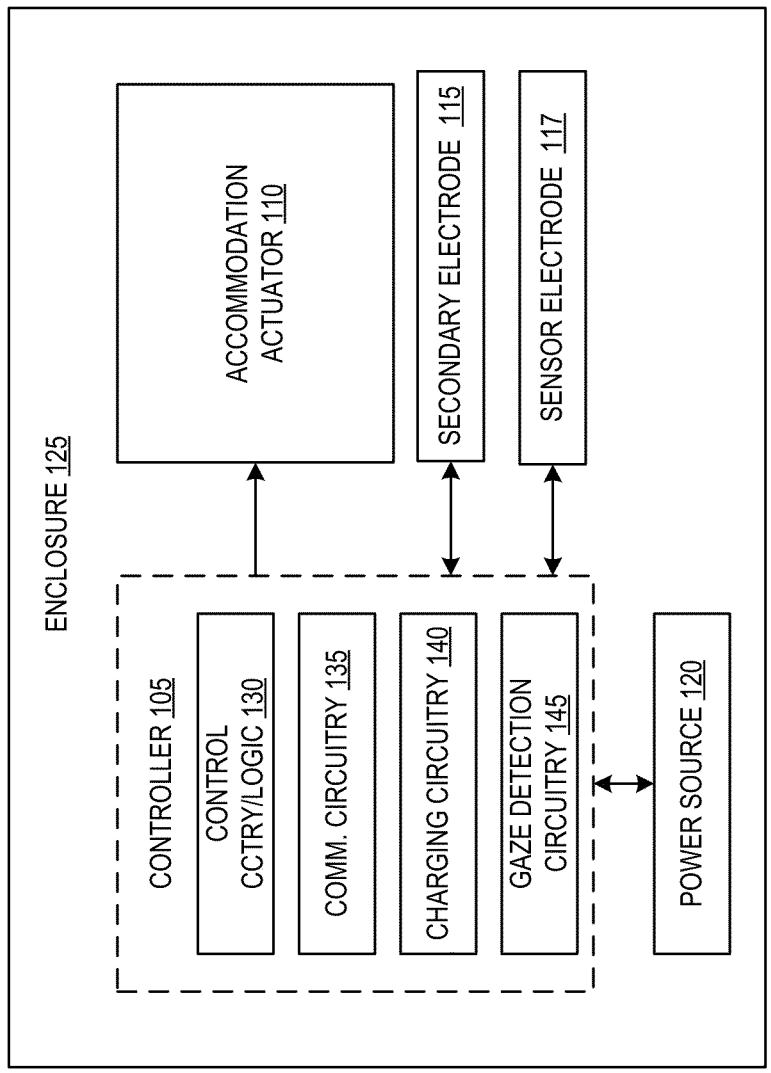
FIG. 1 is a functional block diagram of an ophthalmic device, in accordance with an embodiment of the disclosure.

Embodiments of an apparatus, system, and method of operation for self-testing an impedance sensor and sensor electrode are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The operation of an accommodating ophthalmic device (e.g., contact lens, intraocular lens, or other eyewear) requires a control mechanism for determining when and how much accommodation (optical power adjustment) is needed at a given moment. This accommodation control may be manual, fully automatic, or a hybrid of the two schemes. In some cases, the amount of accommodative optical power needed may be inferred from determining a user's direction of gaze. For example, if both user's eyes pivot inward or down, it may be inferred that the user is using their near-distance vision. Correspondingly, if the user's eyes are looking straight forward or up, it may be inferred that they are using their far-distance vision. A determination of an amount that a user's eyelids overlap the ophthalmic device may be used as a proxy for determining their gaze direction from which an accommodation setting may be correlated and used for feedback control to an accommodation actuator (i.e., variable power dynamic lens).

In some designs for eye-mountable devices (e.g., contact lens, IOL, etc.), the sensing of eyelid overlap is performed by photodetection to determine whether light is being prevented from reaching a photodiode that is disposed in an eye-mountable device (EMD). This use of light-based sensing has certain drawbacks - e.g., due to the wide dynamic range of ambient light in many typical environments. As an alternative to photodetector sensing, other EMD designs rely on a type of capacitive sensing, similar to that used in touchscreen technologies, to detect a capacitance of an eyelid. However, this type of capacitive sensing tends to have problems distinguishing a user's eyelid from the presence of a film of tear fluid (or "tear film") over the user's eye. It is believed that the conductivity of a tear film tends to block, or severely limit, the impact that a capacitance of a user's eyelid may otherwise have on dielectric and/or electric field properties of a fully-encapsulated capacitance sensor within an EMD. The tear film is believed to be a source of error in detecting eyelid capacitance.

Accordingly, embodiments described herein use an impedance sensor implemented with an oscillator circuit that correlates an oscillation condition influenced by an impedance of an inductive sensor electrode to an amount of eyelid overlap, which in turn may be used to correlate to an accommodation setting for controlling an accommodation actuator, may be used to activate/deactivate the accommodation actuator, may be used to sense blink commands for triggering accommodation, or otherwise. This impedance sensing uses a wireless, inductive coupling technique along with an oscillator to efficiently distinguishing between the presence of a tear film and eyelid overlap.

Since the impedance sensor and sensor electrode perform an important function for such an accommodating ophthalmic device, it is also important to be able to efficiently and accurately test the structural and/or functional integrity of these feedback control elements. Embodiments of the built-in self-test (BIST) mechanism described herein can repeatably test the impedance sensor and sensor electrode during manufacturing, production, overnight charging, or even in-situ while the end user is wearing the ophthalmic device. The described BIST mechanism is capable of testing whether the sensor electrode is properly connected to the control circuitry during manufacture and can monitor material changes in the sensor electrode overtime via measuring and tracking baseline impedance measurements.

Embodiments described herein apply a wireless impedance change using an adjacent secondary electrode (e.g., antenna electrode used for backscatter communications). By leveraging the wireless inductive coupling between the sensor electrode and an adjacent secondary electrode, it is possible to impart, load, or otherwise influence an impedance change on the sensor electrode. In other words, by changing the impedance of an adjacent secondary electrode between one or more predetermined impedance states, this known load is wirelessly imparted to the sensor electrode like a transformer and may serves as a reference test load during testing. In the example where the secondary electrode is a backscatter loop antenna, the switching circuitry may be opened and closed to select predetermined impedance states, which are inductively coupled to the sensor electrode in an efficient and repeatable way.

This wireless loading technique provides a number of advantages. First, it is self-contained and does not require external, mechanically moving parts. Second, without mechanical moving part, the BIST mechanism is expected to be highly reliable. Third, implementing the secondary testing electrode with an already present component, such as a backscatter loop antenna, is cost efficient and saves valuable space in a compact device such as a contact lens. Fourth, the test is highly repeatable and less susceptible to error than using load sources external to the ophthalmic device. Fifth, the test can be performed during manufacturing or in-situ when the ophthalmic device is being used in or on the eye.

Although the structures and methods described herein are particularly well suited for use in an ophthalmic device to test the accommodative feedback control circuitry, it should be appreciated that these structures and techniques may be used in other devices. In fact, any device that includes an impedance sensor coupled to a sensor electrode for sensing a wireless load may benefit from the described techniques for self-testing the operational and structural integrity of the impedance sensor, the sensor electrode, and/or the connection between the impedance sensor and the sensor electrode.

FIG. 1 is a functional block diagram of an ophthalmic device 100, such as a smart contact lens, including circuitry to detect whether at least a portion of ophthalmic device 100 is being overlapped by an eyelid of a user. Detection of this type of overlap (for brevity, referred to herein simply as "eyelid overlap") may be used, for example, for feedback control of an accommodation actuator.

The illustrated embodiment of ophthalmic device 100 includes a controller 105, an accommodation actuator 110, a secondary electrode 115, a sensor electrode 117, and a power source 120 all sealed within an enclosure 125. The illustrated embodiment of controller 105 includes control circuitry/logic 130, communication circuitry 135, charging circuitry 140, and gaze detection circuitry 145. It should be appreciated that FIG. 1 is a functional diagram and some of the illustrated components and circuitry may be implemented in hardware, software, or a combination of both. Furthermore, the physical components that implement the illustrated functions may be centralized as illustrated, or distributed. In one embodiment, controller 105 is implemented within a custom application specific integrated circuit (ASIC) that is mounted on an annular substrate within enclosure 125.

The enclosure material, represented by enclosure 125, may function as a light transmissive lensing material and may form, at least in part, a sealed enclosure in which is disposed circuitry of ophthalmic device 100. The dielectric enclosure material may be fabricated of a variety of materials biocompatible for direct contact with a human eye, such as a polymeric material, a hydrogel, PMMA, silicone based polymers (e.g., fluoro-silicon acrylate), or otherwise. Enclosure material 125 may be in the form of a round lens with a concave curvature configured to mount to a corneal surface of an eye. The electronics may be disposed upon a substrate embedded within the one or more enclosure materials near a periphery of ophthalmic device 100 to avoid interference with incident light received closer to the central region of the cornea.

Control circuitry/logic 105 represents miscellaneous components for orchestrating the operation of ophthalmic device 100. For example, control circuitry/logic 105 may be implemented with a microcontroller, on-board memory storing various software instructions, and may also include hardware logic configured to perform specific functions. Communication circuitry 135 may include RF electronics to receive, and in some embodiments also transmit, wireless data over secondary electrode 115. In one embodiment, communication circuitry 135 is a RF identification tag and secondary electrode 115 is a backscatter loop antenna. Charging circuitry 140 may include RF power rectification circuitry to harvest power from an RF carrier wave incident upon secondary electrode 115 and charge power source 120 (e.g., on-board battery, storage capacitor, etc.). Gaze detection circuitry 145 includes embodiments of the impedance sensor described herein, which selectively forms an oscillator with sensor electrode 117 to sense an amount of eyelid overlap and provide feedback control to accommodation actuator 110. Accommodation actuator 110 is a dynamic lens, such as a liquid crystal (LC) cell, a multi-layer LC diffractive lensing structure, an electrowetting lens, or otherwise.

Figure 2A:
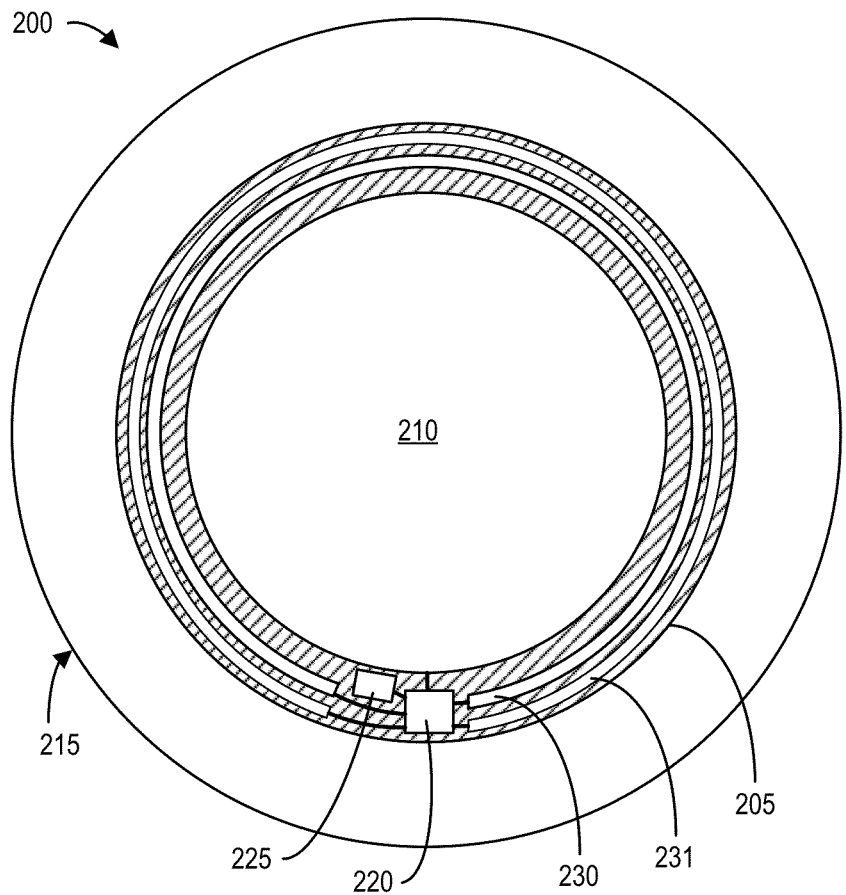
FIGS. 2A & 2B are plan and perspective view illustrations of a contact lens, in accordance with an embodiment of the disclosure.
Figure 2B:
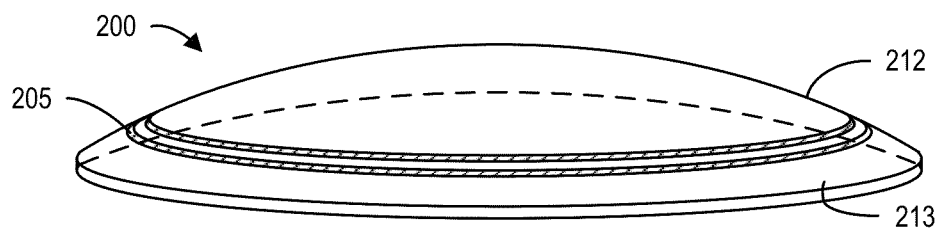

FIGS. 2A and 2B are illustrations of a contact lens system 200 including a dynamic diffractive liquid crystal lens, in addition to a gaze detection circuit that utilizes eyelid overlap sensing according to an embodiment of the disclosure. System 200 is one possible implementation of ophthalmic device 100 illustrated in FIG. 1. The illustrated embodiment of contact lens system 200 includes an annular substrate 205, a dynamic lens 210, an enclosure 215, a controller 220, a power source 225, a sensing electrode 230, and a secondary electrode 231. Enclosure 215 has a size and shape that mounts over the cornea of an eye. In the illustrated embodiment, enclosure 215 includes an anterior side 212 having a convex shape and a posterior side 213 having a concave shape. Of course, contact lens system 200 may assume other shapes and geometries including a piggyback configuration that attaches to a surface of an eye-mountable carrier substrate having an overall shape that resembles a conventional contact lens.

In the illustrated embodiment, secondary electrode 231 is a backscatter loop antenna that encircles sensor electrode 230, which is also an inductive loop. Sensing electrode 230 is one possible implementation of sensing electrode 117 while secondary electrode 231 is one possible implementation of secondary electrode 115. As illustrated, both electrodes 230 and 231 encircle dynamic lens 210 and couple at either opposing ends to controller 220. In one embodiment, sensor electrode 230 is a differential electrode with its opposite ends coupled to differential inputs of an impedance sensor disposed within controller 220.

Figure 3:
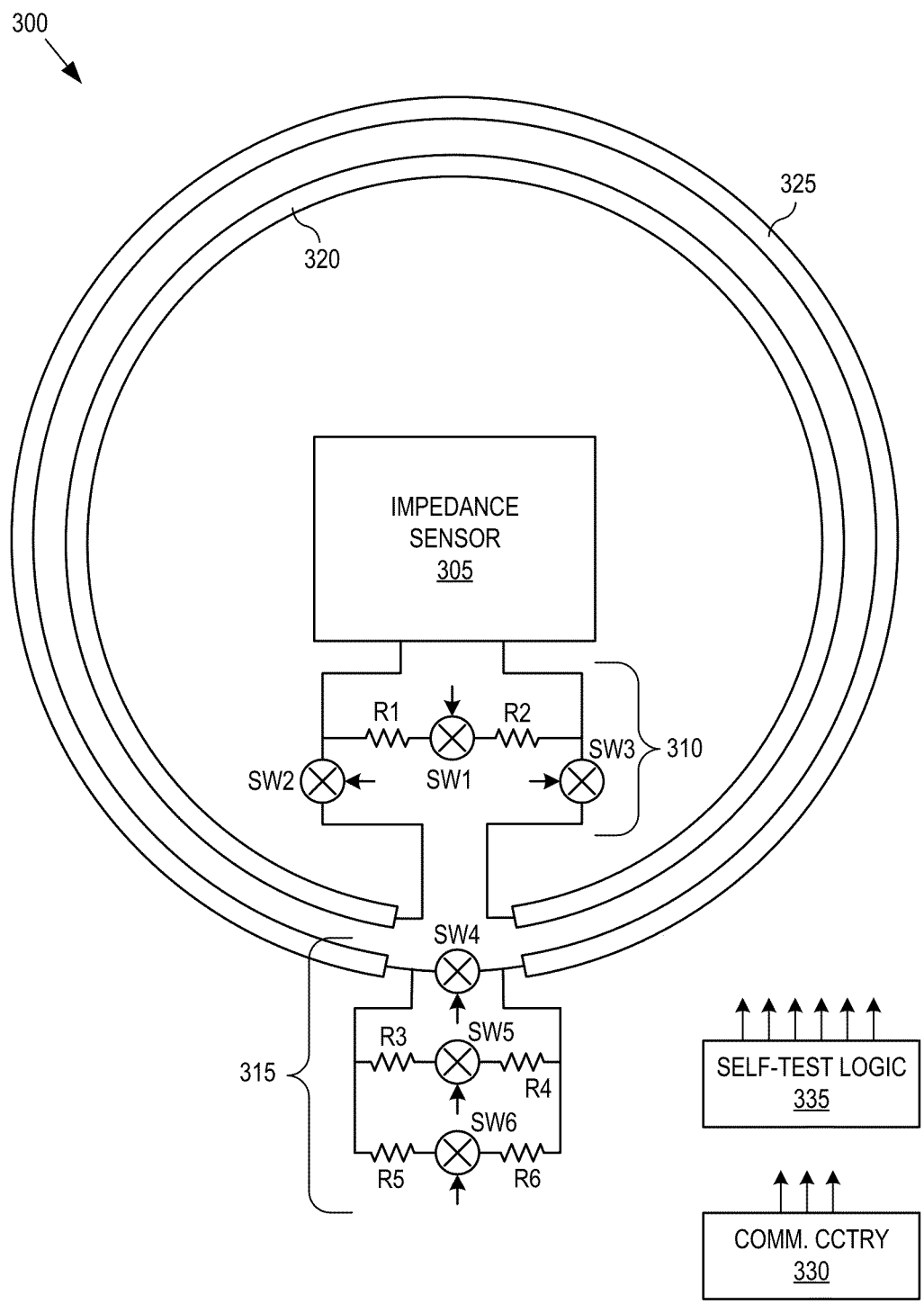
FIG. 3 illustrates functional components and self-test circuitry for testing operational/structural health of an impedance sensor and/or a sensor electrode, in accordance with an embodiment of the disclosure.

FIG. 3 illustrates functional components 300 for testing operational/structural health of an impedance sensor and/or a sensor electrode, in accordance with an embodiment of the disclosure. Components 300 include impedance sensor 305, switch networks 310 and 315, a sensor electrode 320, a secondary electrode 325, communication circuitry 330, and self-test logic 335. The illustrated embodiment of switch network 310 includes resistors R1 and R2 along with switches SW1, SW2, and SW3. The illustrated embodiment of switch network 315 includes resistors R3, R4, R5, and R6 along with switches SW4, SW5, and SW6. In on embodiment, impedance sensor 305 is included within gaze detection circuitry 145 of FIG. 1, sensor electrode 320 represents a possible implementation of sensor electrode 117, secondary electrode 325 represents a possible implementation of secondary electrode 115, communication circuitry 330 corresponds to communication circuitry 135, and self-test logic 335 may be included within control circuitry/logic 130. In one embodiment, impedance sensor 305, self-test logic 335, and communication circuitry 330 are integrated into controller 220 illustrated in FIG. 2A. In yet another embodiment, switch networks 310 and 315 are also integrated into controller 220 thus providing a compact and reliable solution.

Impedance sensor 305 couples to sensor electrode 320 to measure an impedance across opposite ends of sensor electrode 320. In one embodiment, impedance sensor 305 is a differential sensor having differential inputs coupled to sensor electrode 320. Sensor electrode 320 may be implemented with a conductive trace routed in the shape of an inductive loop. As described below, this loop is capable of inductively coupling with an external load. During regular operation, the external load varies based upon the proximity of an external object, such as eyelid coverage. During a self-test mode, the proximity of sensor electrode 320 to secondary electrode 325 enables these electrodes to couple in a manner similar to primary and secondary windings of a transformer. This electrode-to-electrode wireless coupling is leveraged during the self-test mode to inductively load sensor electrode 320 with a predetermined wireless load by placing secondary electrode 325 into a predetermined impedance state. Impedance measurements by impedance sensor 305 can then be compared to baseline impedance measurements or a threshold impedance range to determine whether impedance sensor 305 is correctly functioning, to determine whether the physical integrity or material properties of sensor electrode 320 have degraded or changed, or whether impedance sensor 305 has a proper electrical connection to sensor electrode 325.

In the illustrated embodiment, switch network 315 is coupled across the opposite ends of secondary electrode 325 to selectively changes its impedance. Switch network 315 may include just a single switch (e.g., switch SW4) or multiple switches (e.g., SW4-SW6) coupled in parallel across the opposite ends of secondary electrode 325. In the illustrated embodiment, switch SW5 is coupled in series between resistors R3 and R4 while switch SW6 is coupled in series between resistors R5 and R6. In one embodiment, resistors R3 and R4 are balanced impedances (e.g., substantially equivalent resistances) and similarly resistors R5 and R6 are balanced impedances. In other embodiments, resistors R3-R6 may all be the same or different impedances. Of course, switch network 315 may include more or less impedances and switches coupled in parallel than illustrated in FIG. 3. Furthermore, switch network 315 may also include reactive impedances.

Resistors R3-R6 facilitate placing secondary electrode 325 in different impedance states to provide impedance granularity during the self-test mode. In contrast, switch SW4 alone only provides a short-circuited impedance state or an open-circuited impedance state for secondary electrode 325. One or more of these impedance states may be used as a predetermined impedance state during self-testing.

During other operational states of components 300, communication circuitry 330 may modulate one or more of switches SW4, SW5, and SW6 to modulate the impedance of secondary electrode 325 for the purposes of backscatter communication. In other words, secondary electrode 325 may serve as a backscatter loop antenna and is timeshared between communication circuitry 330 and self-test logic 335. During the self-test mode, self-test logic 335 (or communication circuitry 330) adjust switches SW4-SW6 to one or more predetermined settings to place the backscatter loop antenna into a predetermined impedance state. In one embodiment, switches SW4-SW6 are successively cycled through different combinations of opened and closed states to acquire multiple different impedance measurements by impedance sensor 305. These multiple measurements may collectively increase noise rejection, or otherwise improve the signal-to-noise ratio or quality of the overall self-test.

Impedance sensor 305 may be permanently coupled to the opposite ends of sensor electrode 320 (e.g., omitting switches SW2 and SW3) or selectively coupled via switching network 310. Switches SW2 and SW3 operate as isolation switches that open-circuit to electrically disconnect, or otherwise isolate, impedance sensor 305 from sensor electrode 320. In the illustrated embodiment, isolation switches SW2 and SW3 are coupled between the differential inputs of impedance sensor 305 and the opposite ends of sensor electrode 320.

The illustrated embodiment of switching network 310 further includes a shunting path for testing impedance sensor 305 electrically. This shunting path includes switch SW1 (referred to as a shunting switch) coupled in series with resistors R1 and R2. The shunting path is coupled across the differential inputs of impedance sensor 305. When the shunting switch SW1 is open-circuited, the shunting path is disabled. When the shunting switch SW1 is closed-circuited, the series coupled test load of R1+R2 is presented to impedance sensor 305. In one embodiment, R1 and R2 are substantially equivalent resistances, and in some embodiments, may also include reactive loads from one or more capacitors or inductors to more broadly check the ability of impedance sensor 305 to measure a reactive or complex load.

The series coupled test load may operate as a baseline reference load for calibration or validation of impedance sensor 305. In one embodiment, the shunting path may be integrated into the ASIC (e.g., controller 220) that also includes impedance sensor 305. While the shunting path may not test the wireless nature of sensor electrode 320, or even whether sensor electrode 320 is properly coupled to impedance sensor 305, it can still provide a validation of impedance sensor 305 and help isolate the location of a detected failure (e.g., upstream vs downstream of the shunting path). Switches SW1-SW3 may be coupled to and controlled by self-test logic 335.

Figure 4A:
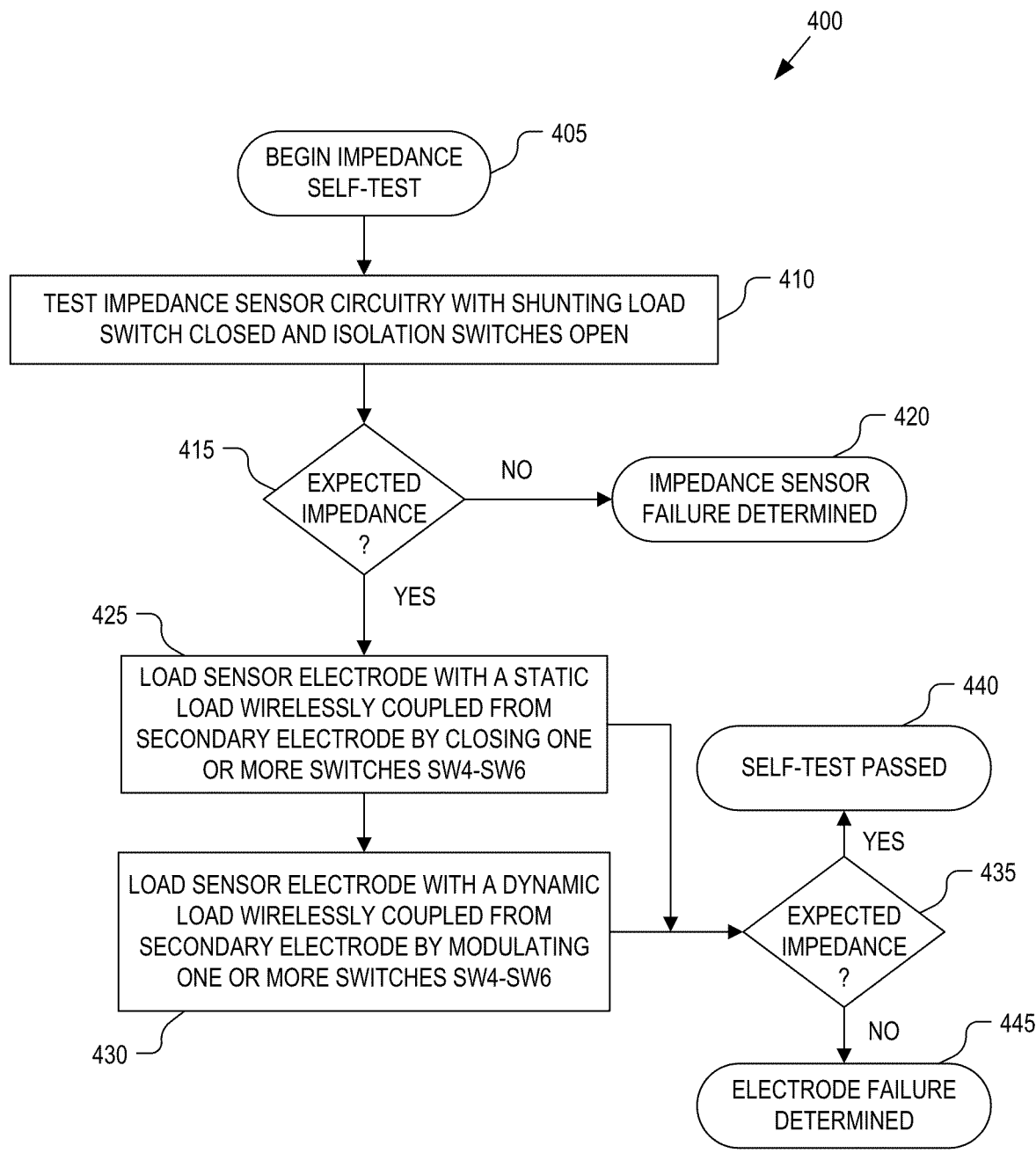
FIG. 4A is a flow chart illustrating a self-test mode for testing the operational/structural health of an impedance sensor and/or a sensor electrode, in accordance with an embodiment of the disclosure.

FIG. 4A is a flow chart of a process 400 for testing the operational/structural health of impedance sensor 305 and/or a sensor electrode 320, in accordance with an embodiment of the disclosure. The order in which some or all of the process blocks appear in process 400 should not be deemed limiting. Rather, one of ordinary skill in the art having the benefit of the present disclosure will understand that some of the process blocks may be executed in a variety of orders not illustrated, or even in parallel.

Process 400 begins at process block 405 with impedance sensor 305 enabled. In a process block 410, impedance sensor 305 self-tests just its own operation using the shunting path. In other words, self-test logic 335 closes the shunting switch SW1 while open-circuiting isolation switches SW2 and SW3. With the shunting load of R1 + R2 presented across the differential inputs of impedance sensor 305, the impedance of the shunting load is measured and compared against a baseline value or threshold impedance range that is expected for R1 + R2. If the measured impedance falls outside of the expected threshold impedance range (decision block 415), then self-test logic 335 determines that the self-test has failed with a defect in impedance sensor 305 (process block 420). If, however, the measured impedance falls within the expected threshold impedance range (decision block 415), then this first subtest is passed and self-test logic 335 determines that impedance sensor 305 is operating within specified parameters and proceeds to the next subtest. It should be appreciated that the subtest of process block 410 may also include measuring and comparing impedances when isolation switches SW2 and SW3 are close-circuited. In fact, in some embodiments, isolation switches SW2 and SW3 may be omitted.

In a process block 425, self-test logic 335 close-circuits isolation switches SW2 and SW3 while open-circuiting shunting switch SW1 and wirelessly presents a static load onto sensor electrode 320 via secondary electrode 325. The static load may include any combination of open and closed switches SW4-SW6 within switching network 315. In one embodiment, switch SW4 is close-circuited while switches SW5 and SW6 are open-circuited. Other combinations, or even successive multiple combinations, may be used to present different successive static wireless loads for measurement and threshold comparisons. If the tested impedance(s) measured by impedance sensor 305 fall within expected threshold impedance ranges, (decision block 435), then the self-test is passed (process block 440) and impedance sensor 305, sensor electrode 320 along with the connection between impedance sensor 305 and sensor electrode 320 are all validated. Of course, if one or more of the measured test impedances fall outside expected threshold ranges (decision block 435), then sensor electrode 320 and/or the connection between sensor electrode 320 and impedance sensor 305 may be deemed to have failed (process block 445). Sensor electrode 320 may fail from material defects due to aging or mechanical stresses. The connection between sensor electrode 320 and impedance sensor 305 may fail as a result of a manufacturing error, operational fatigue, etc.

In one embodiment, a third subtest may further be executed in a process block 430. This third subtest may present dynamic or time varying wireless loads to sensor electrode 320 via secondary electrode 325. The dynamic load may be achieved by modulating one or more switches SW4-SW6. In one embodiment, a high frequency modulation scheme, variable duty cycle, or otherwise may be used to test the dynamic response of impedance sensor 305. Again, if the measured test impedances fall outside expected threshold impedance ranges, then the self-test is deemed failed (process block 445). If the measured test impedances fall within expected threshold impedance ranges, then the self-test is passed (process block 440).

Figure 4B:
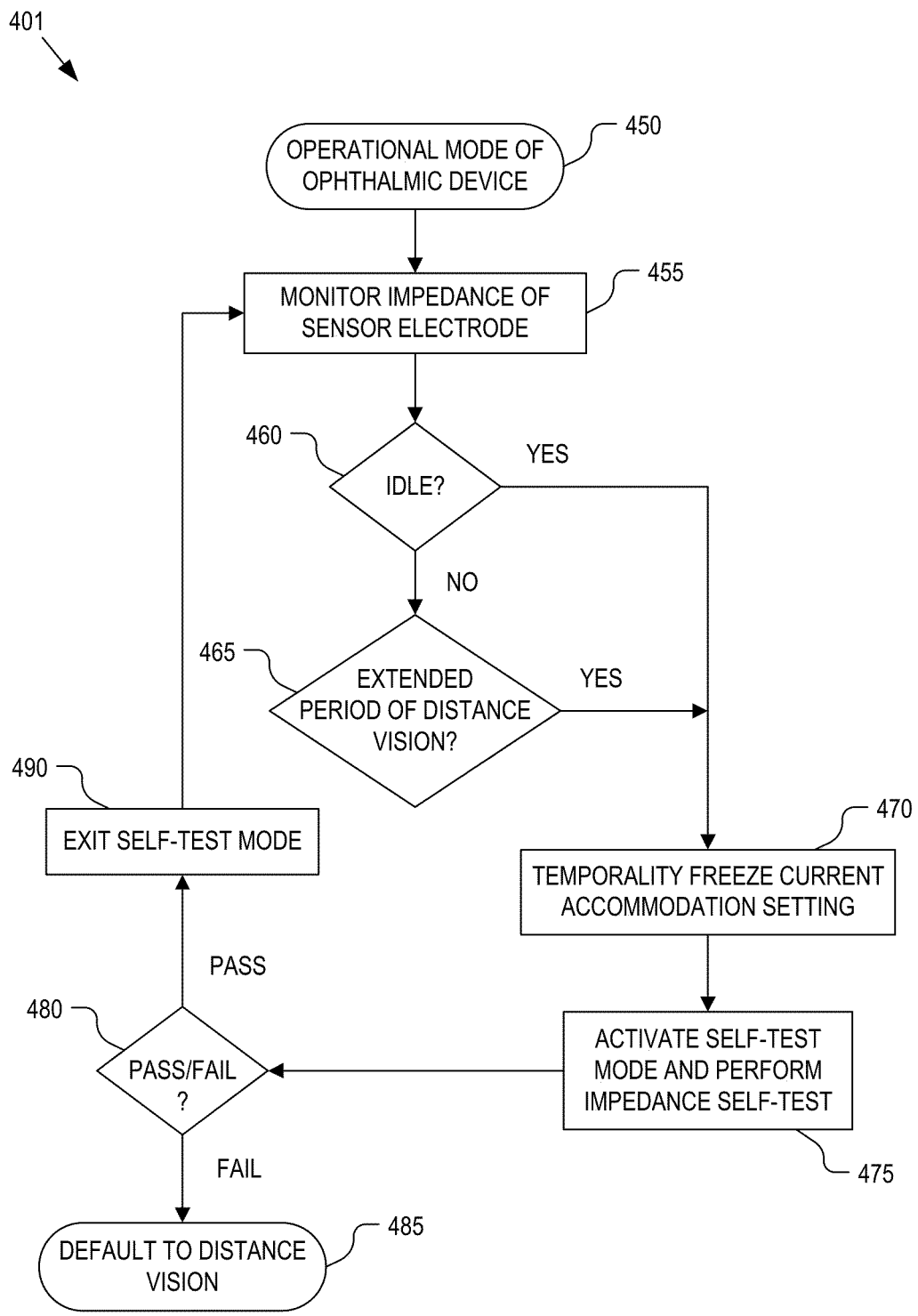
FIG. 4B is a flow chart illustrating when to transition an ophthalmic device from an operational mode to a self-test mode, in accordance with an embodiment of the disclosure.

FIG. 4B is a flow chart illustrating a process 401 for determining when to transition ophthalmic device 100 (or contact lens system 200) from an operational mode to a self-test mode, in accordance with an embodiment of the disclosure. The order in which some or all of the process blocks appear in process 401 should not be deemed limiting. Rather, one of ordinary skill in the art having the benefit of the present disclosure will understand that some of the process blocks may be executed in a variety of orders not illustrated, or even in parallel.

In a process block 450, ophthalmic device 100 is operating in a regular mode of operation. In one embodiment, the regular mode of operation uses impedance sensor 305 to monitor the impedance of sensor electrode 320 (process block 455) as indicative of eyelid overlap, which is a proxy for gaze direction and may be used to provide feedback control over accommodation actuator 110 (or 210). If changes in measured impedance of sensor electrode 320 are determined to be idle (decision block 460), then self-test logic 335 may take this opportunity to initiate an on-demand or periodic self-test. The determination that sensor electrode 320 is idle may be based upon one or more thresholds. For example, an idle determination may be based upon successive impedance measurements that do not deviate greater than a threshold magnitude (e.g., do not deviate greater than an expected noise level) for a threshold period of time.

By determining that sensor electrode 305 is idle, it is assumed that auto-accommodation can be temporarily suspended while a self-test is performed. Accordingly, the current accommodation setting (i.e., optical power of accommodation actuator 110) is temporarily frozen (process block 470), while the self-test mode is activated to perform an impedance self-test (process block 475). If the self-test passes (decision block 480), then process 401 exits the self-test mode (process block 490) and impedance sensor 305 resumes monitoring the impedance of sensor electrode 320 for auto-accommodation feedback control.

If the impedance measurement are not idle (decision block 460) but are otherwise measuring impedance values indicative of far-distance vision for an extended period of time that exceeds a threshold period of time (decision block 465), then the test mode may also be activated (process block 475) after freezing the accommodation setting for accommodation actuator 110 in a far-distance vision setting (process block 470). Other threshold tests may be used to take advantage of other low demand periods for auto-accommodation to enter into the self-test mode.

If a self-test is deemed to have failed (decision block 480), then self-test logic 335 may force accommodation actuator 110 into a default mode. In one embodiment, the default mode is an optical power setting for accommodation actuator 110 associated with a given user's far-distance vision. Defaulting to distance vision is considered a safe default mode for many activities including driving.

Figure 5:
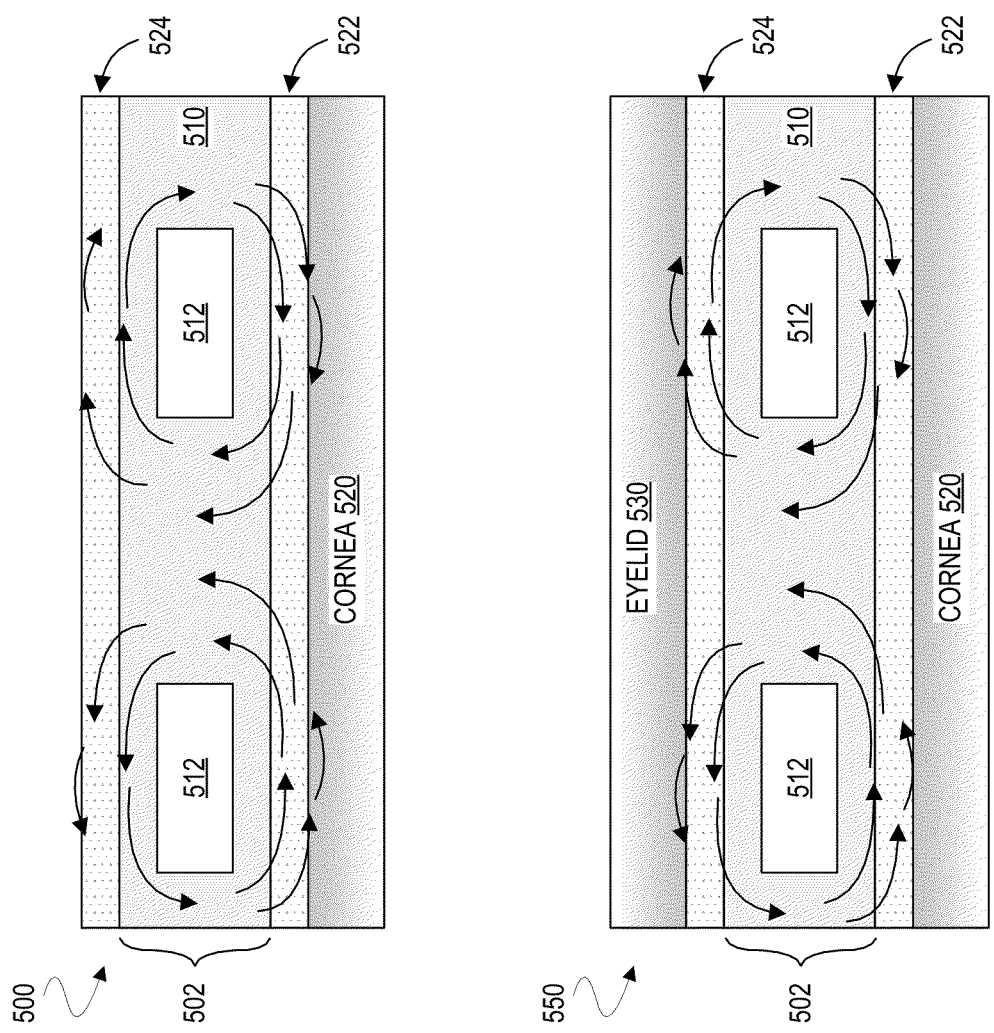
FIG. 5 illustrates cross-sectional views variously representing an ophthalmic device exposed or overlapped by an eyelid, in accordance with an embodiment of the disclosure.

FIG. 5 shows cross-sectional views – during respective states 500, 550 -of a user's eye while that user is wearing an ophthalmic device 502 (e.g., ophthalmic device 100 or contact lens system 200) according to an embodiment. Gaze detection circuitry including an impedance sensor may be fully encapsulated within an encapsulation material 510 of the ophthalmic device 502. Such encapsulation may aid in preventing moisture ingress during the operating lifetime of ophthalmic device 502. Operation of the impedance sensor, which forms an oscillator when connected with sensor electrode 512, may exploit the formation of a capacitive link which extends between a fully encapsulated electrode of the sensor circuit and the surface of a tear film. For brevity, this type of capacitive link is referred to herein as "lens capacitance."

A tear film may be conductive of a current that is induced by the oscillator. The effect of such conductivity on operational characteristics of the oscillator may change over time with the changing external environment - e.g., due to any additional conductance of a biological material (such as the eyelid) that comes in contact with the tear film. The extent to which an eyelid overlaps the sensor circuit may affect a resistivity of a current path that is in parallel with the tear film. In order to efficiently measure bio-conductance/bio-resistance of a tear film (in combination with that resulting from any eyelid overlap), some embodiments variously provide an inductive element that, for example, is coupled in parallel with an in-series combination of lens capacitance Cp and two parallel resistances from the tear film $R_T$ and eyelid $R_E$. During a resonance state of the oscillator, such an inductance element may cancel out or otherwise significantly offset an impedance provided with the lens capacitance Cp. Therefore, at the resonance state of the sensor circuit, the frequency of oscillation may be automatically determined as a resonance for a combination of an inductor element L1 and the lens capacitance Cp, effectively exposing a total amount of resistance provided by the tear film $R_T$ and eyelid $R_E$, if present, - e.g., where sensing of such resistance is not obscured by the impedance of the lens capacitance Cp. This resistance may directly correlate with, and be sensed by determining, a bias setting (e.g., a minimum amount of current) needed to startup oscillation of an oscillator. Accordingly, the impedance sensors described herein sense or measure the impedances $R_T$ and $R_E$ by determining a bias setting (e.g., setting of a current source) of an oscillator circuit at the onset of an oscillation condition.

The inductance element L1 may be formed, for example, with a ring-like configuration for the sensor electrode 512 that also contributes to lens capacitance. As mentioned, the impedance sensor of the gaze detection circuitry forms an oscillator circuit when selectively coupled to sensor electrode 512 that is configured to induce oscillation (resonance) with the sensor electrode that contributes to the lens capacitance. An amount of current required to achieve oscillation startup (e.g., onset of an oscillation condition) may be proportional to the amount of resistance across at least a portion of the tear film. Accordingly, a measurement of the startup current necessary to induce the oscillation condition is a proxy or measurement of the impedance across sensor electrode 512. At a time when an eyelid overlaps at least a portion of the sensor electrode 512, the resistance across an underlying portion of tear film may be relatively low, as compared to when there is relatively less (or no) eyelid overlap. A level of such bio-resistance may be measured in some embodiments by determining a threshold amount of current required to start oscillator of sensor circuitry.

During states 500 and 550, ophthalmic device 502 is disposed on a cornea 520 of the user's eye, wherein a tear film 522 extends between a cornea 520 of the eye and enclosure material 510 of ophthalmic device 502. Another tear film 524 may extend across an upper surface of enclosure material 510. State 500 represents a time when, as compared to state 550, an eye of the user is relatively more open. During state 550, an eyelid 530 of the user overlaps a surface area of enclosure material 510 that is larger than any area of enclosure material 510 that might be overlapped by eyelid 530 during state 500.

Figure 6:
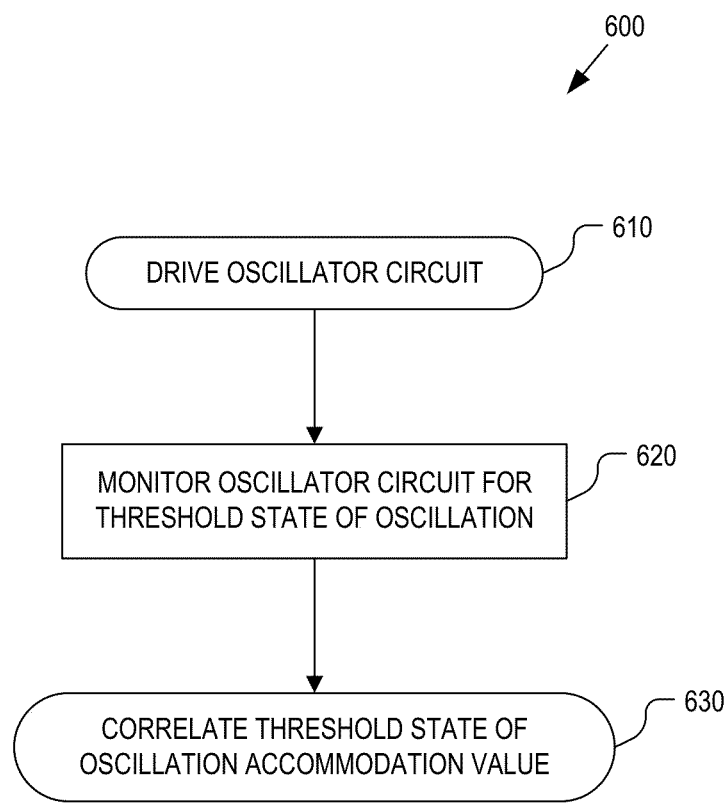
FIG. 6 is a flow chart illustrating operation of an impedance sensor during an operational mode to provide feedback control to an accommodation actuator, in accordance with an embodiment of the disclosure.

FIG. 6 is a flow chart illustrating a process 600 of operation of an impedance sensor 700 (see FIG. 7) during an operational mode to provide feedback control to an accommodation actuator, in accordance with an embodiment of the disclosure. Impedance sensor 700 represent one possible implementation of impedance sensor 305. However, it should be appreciated that impedance sensor 700 is just one possible implementation and other types of impedance sensors may be implemented. Process 600 is described with reference to impedance sensor 700.

Figure 7:
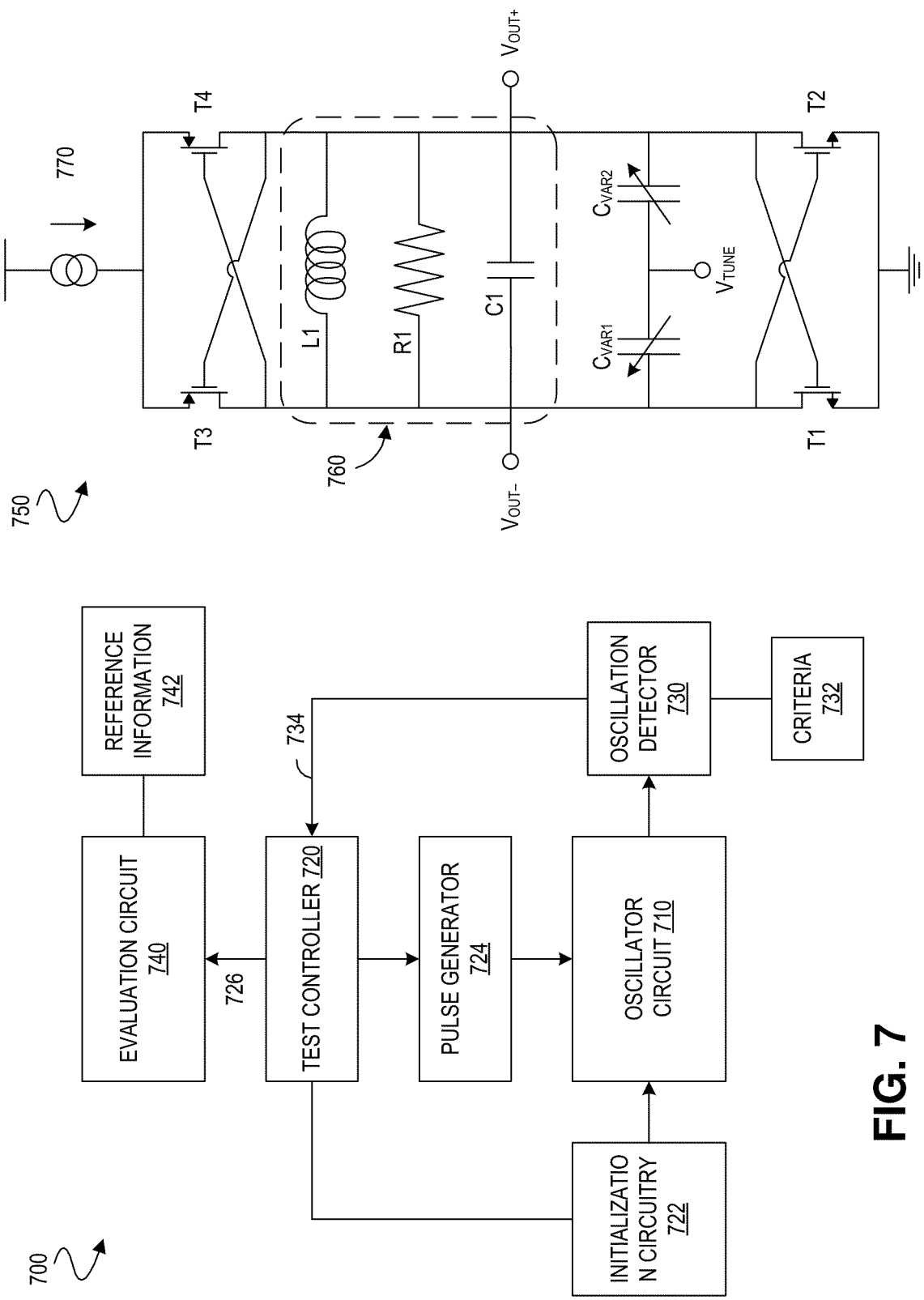
FIG. 7 illustrates functional components and oscillator circuitry for implementing a demonstrative impedance sensor, in accordance with an embodiment of the disclosure.

FIG. 7 shows features of a sensor system 700 to detect eyelid overlap according to an embodiment. Sensor system 700 may be adaptable for encapsulation within one or more of a smart contact lens or other ophthalmic device. While the ophthalmic device is mounted on an eye of a user, a first tear film may be disposed by the user over a forward-facing side of the ophthalmic device (e.g., where an eyelid of the user may variously overlap the forward-facing side at different times). A second tear film may be similarly disposed between the ophthalmic device and a cornea of the user's eye.

Process 600 may include, at 610, driving an oscillator circuit which includes an electrode disposed within a sealed enclosure formed by a lens of the ophthalmic device. The driving at 610 may result in an electromagnetic field being emitted from the lens and into an environment outside the ophthalmic device. The electromagnetic field may be influenced by an amount to which the electrode is overlapped by an eyelid of a user wearing the ophthalmic device. In turn, this influence may affect whether an oscillator circuit will exhibit an oscillation response to a perturbation.

Referring again to FIG. 7, sensor system 700 includes an oscillator circuit 710 that is coupled to conduct charge that facilitates an electromagnetic interaction with structures external to the ophthalmic device - e.g., where such structures include one or more adjoining tear films, a cornea of the user and/or any overlapping portion of the user's eyelid. For example, oscillator circuit 710 may include an electrode (symbolically represented by L1) extending in the ophthalmic device.

In an embodiment, method 600 further comprises, at 620, monitoring the oscillator circuit for a threshold state of oscillation. For example, the driving at 610 may comprise driving the oscillator circuit with a variable current, wherein the monitoring at 620 includes monitoring the oscillator circuit for the threshold state of oscillation while successively changing the variable current.

System 700 further includes circuitry to detect an oscillation of oscillator circuit 710, wherein the oscillation is based at least in part on electromagnetic interaction each between a tear film and an electrode of oscillator circuit 710. In the illustrative embodiment shown, such circuitry of system 700 includes a test controller 720, initialization circuitry 722, pulse generator 724 and oscillation detector 730.

The monitoring at 620 may include interrogating the circuit, which in this context refers to testing for an oscillation response (if any) to a particular input bias current. Such interrogating may identify whether a circuit response satisfies one or more evaluation conditions for being considered an oscillation state. In an embodiment, the monitoring at 620 includes successively interrogating the circuit - e.g., where some or all such interrogations each use a different respective amount of the input bias current in attempting to induce circuit oscillation. Adjusting the input bias current - where a next bias current amount is to be set for a next one of the successive circuit interrogations - may be performed intelligently based on one or more previous interrogation results.

FIG. 7 also shows a circuit diagram 750 including RLC oscillator circuitry 760 that models a combination of oscillator circuit 710 and structures, external to an ophthalmic device including system 700, that are to interact electromagnetically with oscillator circuit 710. RLC oscillator circuitry 760 includes an inductor L1 (e.g., sensor electrode), a resistor R1 and a capacitor C1 coupled in parallel with each other between nodes $V_{out-}$, $V_{out+}$. L1 represents an inductance provided by oscillator circuit 710, and R1 represents a combination of resistances variously provided, along different signal paths, within and/or between oscillator circuit 710 and a surrounding environment. C1 represents a combination of capacitances variously provided along some or all such different signal paths. R1 may vary over time based at least in part on an amount by which an eyelid overlaps system 700.

Circuit diagram 750 includes additional circuitry coupled to RLC oscillator circuitry 760, where such additional circuity facilitates testing to detect eyelid overlap. Such testing may include providing one or more inputs to oscillator circuit 710 and determining whether a resulting oscillation at oscillator circuit 710 takes place. For example, additional circuity to provide such one or more inputs may include some or all of a current source 770, circuitry (not shown) coupled to provide a tuning (e.g., biasing) voltage $V_{tune}$ and circuitry (not shown) coupled to operate one or more variable capacitors $C_{var1}$, $C_{var2}$. In the illustrative embodiment, circuitry 760 is coupled across terminals nodes $V_{out-}$, $V_{out+}$, as are capacitors $C_{var1}$, $C_{var2}$, cross-coupled transistors T3, T4 and cross-coupled transistors T1, T2. In particular, $V_{tune}$ may be pre-configured, for one or more successive evaluation cycles, to provide for relatively high capacitance values of $C_{var1}$, $C_{var2}$. Such preconfiguring with $V_{tune}$ may result in a relatively high amount of energy being needed to induce oscillation with RLC oscillator circuitry 760. During an evaluation cycle, circuitry such as that of oscillation detector 730 may detect for some minimal amplitude of a signal, across terminals $V_{out-}$, $V_{out+}$, that might be induced with current source 770. In response to detecting such a minimal amplitude, the circuitry may signal that $V_{tune}$ is to be pulled higher, thus decreasing the capacitance values of $C_{var1}$, $C_{var2}$. In turn, this decreased capacitance will increase the tendency of RLC oscillator circuitry 760 to continue starting up an oscillation state, and will increase a rate of increase of the amplitude across terminals $V_{out-}$, $V_{out+}$. Such a positive feedback method may facilitate an oscillation response such as one to be detected by the monitoring at 620.

Based on the monitoring at 620, process 600 may, at 630, correlate a detected threshold state of oscillation with the amount the eyelid overlaps the ophthalmic device. The correlating at 630 may comprise correlating a level of a variable current, bias voltage and/or other condition of an initialization state with the amount the eyelid overlaps the ophthalmic device.

In one embodiment, test controller 720 operates to implement a test round including multiple successive sample cycles each corresponding to a different respective configuration of oscillator circuit 710 by system 700. For each sample cycle of a test round, test controller 720 may signal to initialization circuitry 722 that oscillator circuit 710 is to be configured with an initialization state corresponding to the sample cycle. For example, initialization of oscillator circuit 710 for each sample cycle may include one or more of bringing $V_{tune}$ to a baseline potential (e.g., ground), turning off current source 770, and pulling nodes $V_{out-}$, $V_{out+}$ each to ground or some other baseline potential.

After oscillator circuit 710 is put into the corresponding initialization state for a given sample cycle, test controller 720 may induce some perturbation of oscillator circuit 710 - e.g., for subsequent sampling to detect whether an oscillation event results from such perturbation. For example, test controller 720 may signal a pulse generator 724 to introduce some spike, step-wave pulse, saw-tooth wave pulse and/or change to an input for oscillator circuit 710.

Whether oscillator circuit 710 exhibits an oscillation response to such a perturbation may depend in part upon the value of R1 (which in turn depends in part on any eyelid overlap of oscillator circuit 710). An oscillation detector 730 is coupled to detect whether an output of oscillator circuit 710 — e.g., a voltage across nodes $V_{out-}$, $V_{out+}$ — satisfies a predefined oscillation threshold criteria and therefore qualifies as an oscillation event. For example, a memory of system 700 may store criteria 732 including oscillation threshold information. Based on such evaluation, oscillation detector 730 may provide to test controller 720 an indication 734 as to whether the corresponding sample cycle resulted in an oscillation event at oscillator circuit 710. Based on indication 734, test controller 720 may determine whether the associated sample cycle corresponds to a threshold condition for inducing oscillation with oscillator circuit 710.

Based on the correlating at 630, process 600 may generate one or more signals identifying an amount of the eyelid overlap. For example, based on the test round, test controller 720 may provide to evaluation circuit 740 a test result 726 indicating one or more oscillation characteristics of oscillator circuit 710. Test result 726 may identify or otherwise indicate an initialization state that — of multiple initialization states — most closely represents a threshold state for inducing oscillation with oscillator circuit 710. Based on test result 726, evaluation circuit 740 may access reference information 742 which, directly or indirectly, corresponds various circuit initialization states each with a different respective amount of eyelid overlap. For example, reference information 742 may specify or otherwise indicate, for each of different amounts of an input current (e.g., by current source 770), a corresponding level of a resistance - such as resistance R1 of circuitry 760 - that is due at least in part to eyelid overlap. Using such correspondences, evaluation circuit 740 may calculate, select or otherwise determine an amount of eyelid overlap corresponding to an amount of resistance that is indicated by test result 726.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. An apparatus, comprising:
a sensor electrode;
an impedance sensor coupled to the sensor electrode to measure a test impedance of the sensor electrode as influenced by an external load;
a secondary electrode disposed adjacent to the sensor electrode to wirelessly couple with the sensor electrode and influence the external load on the sensor electrode;
a first switch coupled to the secondary electrode to selectively change a second impedance of the secondary electrode; and
a controller coupled to the impedance sensor and the first switch, the controller including logic that, when executed, causes the apparatus to perform operations including:
adjusting the first switch to place the secondary electrode in a predetermined impedance state, wherein the predetermined impedance state wirelessly influences the test impedance of the sensor electrode;
measuring the test impedance of the sensor electrode with the impedance sensor while the secondary electrode is in the predetermined impedance state; and
comparing the measured test impedance against a threshold impedance range to perform a self-test.

2. The apparatus of claim 1, wherein the sensor electrode comprises a first loop electrode and the secondary electrode comprises a second loop electrode.

3. The apparatus of claim 2, wherein the secondary electrode encircles the sensor electrode or the sensor electrode encircles the secondary electrode.

4. The apparatus of claim 1, wherein the secondary electrode comprises a backscatter antenna and wherein the controller includes communication circuitry coupled to the first switch to modulate the second impedance during backscatter communications via switching of the first switch.

5. The apparatus of claim 4, further comprising:
first and second resistors coupled in series between opposite ends of the secondary electrode; and
an second switch coupled between the first and second resistors, wherein the second switch selectively changes the second impedance of the secondary electrode when close-circuited.

6. The apparatus of claim 1, further comprising:
first and second resistors coupled in series between differential inputs of the impedance sensor that each couple to respective opposite ends of the sensor electrode; and
a shunting load switch coupled in series between the first and second resistors to selectively shunt the opposite ends of the sensor electrode with the first and second resistors when the shunting load switch is close-circuited.

7. The apparatus of claim 6, further comprising:
first and second isolation switches each coupled between respective ones of the differential inputs and the respective opposite ends of the sensor electrode, wherein the first and second isolation switches selectively isolate the sensor electrode from the impedance sensor when open-circuited.

8. The apparatus of claim 1, wherein the apparatus comprises an ophthalmic device and wherein the impedance sensor, the sensor electrode, and the secondary electrode are disposed within an enclosure that is biocompatible for mounting in or on an eye, the apparatus further comprising:
an accommodation actuator disposed within the enclosure to provide variable optical power to the ophthalmic device,
wherein the controller includes further logic that, when executed, causes the apparatus to perform further operations comprising:
adjusting the optical power of the accommodation actuator based upon an operational impedance of the sensor electrode measured by the impedance sensor, wherein changes in the operational impedance are indicative of changes in a gaze direction or eye blinks when the ophthalmic device is mounted in or on the eye.

9. The apparatus of claim 8, wherein the controller includes further logic that, when executed, causes the apparatus to perform further operations including:
monitoring the operational impedance of the sensor electrode;
determining when the operational impedance of the sensor electrode is idle based upon one or more thresholds;
activating a self-test mode when the operational impedance is determined to be idle; and
temporarily freezing a current optical power of the accommodation actuator while in the self-test mode.

10. The apparatus of claim 8, wherein the controller includes further logic that, when executed, causes the apparatus to perform further operations including:

monitoring the operational impedance of the sensor electrode;

determining when at least the operational impedance of the sensor electrode indicates far-distance vision;

activating a self-test mode after the operational impedance indicates the far-distance vision for a threshold period of time; and temporarily freezing a current optical power of the accommodation actuator while in the self-test mode.

11. The apparatus of claim 8, wherein the controller includes further logic that, when executed, causes the apparatus to perform further operations including:

defaulting the variable optical power of the accommodation actuator to far-distance vision when the self-test fails.

12. A method of self-testing an ophthalmic device including a sensor electrode and a secondary electrode, comprising:

entering the ophthalmic device into a self-test mode;

placing the secondary electrode in a predetermined impedance state, wherein the secondary electrode is disposed adjacent to the sensor electrode within the ophthalmic device and inductively couples with the sensor electrode, wherein the predetermined impedance state wirelessly influences a test impedance across the sensor electrode;

measuring the test impedance across the sensor electrode with an impedance sensor coupled to the sensor electrode while the secondary electrode is in the predetermined impedance state; and comparing the measured test impedance against a threshold impedance range to perform a self-test of at least one of the sensor electrode or the impedance sensor.

13. The method of claim 12, wherein placing the secondary electrode in the predetermined impedance state comprises:

close circuiting a first switch coupled between opposite ends of the secondary electrode.

14. The method of claim 13, wherein the secondary electrode comprises a backscatter loop antenna for communicating with the ophthalmic device, and wherein the method further comprises:

modulating a second impedance of the secondary electrode during backscatter communications via switching of the first switch.

15. The method of claim 13, wherein the first switch is coupled in series between first and second resistors, and wherein the first and second resistors are coupled in series between the opposite ends of the secondary electrode.

16. The method of claim 12, further comprising:

shunting differential inputs of the impedance sensor with a resistive test load selectively coupled across the differential inputs of the impedance sensor;

measuring the resistive test load with the impedance sensor while the test load is shunting the differential inputs; and comparing the measured test load to another threshold impedance range to perform the self-test.

17. The method of claim 16, further comprising:

isolating the sensor electrode from the impedance sensor while measuring the resistive test load to test the impedance sensor independent of the sensor electrode.

18. The method of claim 12, wherein the ophthalmic device further includes an accommodation actuator to provide variable optical power to a user when the ophthalmic device is mounted in or on an eye of the user, the method further comprising:

if the measured test impedance falls outside the threshold impedance range, then determining that the self-test has failed and defaulting the optical power of the accommodation actuator to a far-distance vision optical power for the user.

19. The method of claim 18, further comprising:

adjusting the variable optical power of the accommodation actuator during an operational mode of the ophthalmic device, wherein the adjusting is based upon an operational impedance of the sensor electrode measured by the impedance sensor; and prior to entering the self-test mode from the operational mode, temporarily freezing the variable optical power of the accommodation actuator while performing the self-test.

20. The method of claim 18, wherein entering the ophthalmic device into the self-test mode comprises:

entering the ophthalmic device into the self-test mode when an operational impedance of the sensor electrode measured by the impedance sensor is determined to be idle for a threshold period of time.

21. The method of claim 18, wherein entering the ophthalmic device into the self-test mode comprises:

entering the ophthalmic device into the self-test mode when an operational impedance of the sensor electrode measured by the impedance sensor indicates far-distance vision for a threshold period of time.

22. The method of claim 12, wherein the entering the ophthalmic device into the self-test mode comprises entering the ophthalmic device into the self-test mode in-situ while the ophthalmic device is mounted in or on an eye of a user.

* * * * *